United States Patent [19]

Press

[11] Patent Number: 4,727,145

[45] Date of Patent: Feb. 23, 1988

[54] 2- OR 3- ARYL SUBSTITUTED IMIDAZO [1,2-A]PYRIDINES

[75] Inventor: Jeffery B. Press, Rocky Hill, N.J.

[73] Assignee: Ortho Pharmaceutical Corporation, Raritan, N.J.

[21] Appl. No.: 909,648

[22] Filed: Sep. 22, 1986

[51] Int. Cl.$^4$ .......................................... C07D 471/04
[52] U.S. Cl. .................................................... 546/121
[58] Field of Search ................................. 546/121, 70

[56] References Cited

FOREIGN PATENT DOCUMENTS 0068378 1/1983 European Pat. Off. ............ 546/121
1058258 2/1967 United Kingdom ................ 546/121

Primary Examiner—Richard A. Schwartz
Assistant Examiner—J. Richter
Attorney, Agent, or Firm—Benjamin F. Lambert

[57] ABSTRACT

Novel 2- or 3- aryl substituted imidazo[1,2-a]pyridines and their synthesis are described. The compounds have local anesthetic properties and are useful as local anesthetic agents.

5 Claims, No Drawings

2- OR 3- ARYL SUBSTITUTED IMIDAZO [1,2-A]PYRIDINES

BACKGROUND OF THE INVENTION

1. Field of the Invention

The present invention relates to novel 2- or 3- aryl substituted imidazo[1,2-a]pyridines of general formula:

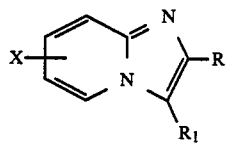  I as described further below. The compounds of formula I are useful as local anesthetic agents.

2. Description of the Prior Art

No examples of local anesthetics with a 2- or 3- aryl substituted imidazo[1,2-a]pyridine structure have been seen in the prior art.

Local anesthetics are drugs which reversibly block nerve conduction near their site of application or injection and thus produce temporary loss of feeling or sensation in a limited area of the body. Local anesthetics are used to prevent pain in surgical procedures, injury, and disease. Local anesthetics can act on any part of the nervous system and on every type of nerve fiber. Since ionic mechanisms of excitability are similar in nerve and muscle, it is not surprising that local anesthetics also have prominent actions on all types of muscular tissue.

Local anesthetics prevent both the generation and the conduction of a nerve impulse. The main site of action is the cell membrane, and there is seemingly little direct action of physiological importance on the axoplasm. The axoplasmic effects that do occur may be secondary to the membrane action.

Known local anesthetics block conduction by interfering with the fundamental process in the generation of a nerve action potential, namely, the large transient increase in the permeability of the membrane to sodium ions that is produced by a slight deplarization of the membrane.

One theory of how local anesthetics block nerve conduction is that they compete with calcium at some site that controls the permeability of the membrane. Local anesthetics also reduce the permeability of resting nerve to potassium as well as to sodium ions.

Adverse reactions to local anesthetics can be divided into two groups: systemic and local adverse reactions. Systemic adverse reactions are usually associated with high blood levels of the drug and usually result from overdosage, rapid systemic absorption, or inadvertant intravenous administration. The reactions usually involve the central nervous and cardiovascular systems. Local adverse reactions to known local anesthetic drugs are either cytotoxic or allergic.

SUMMARY OF THE INVENTION

The present invention is directed to 2- or 3- aryl substituted imidazo[1,2-a]pyridines of the formula

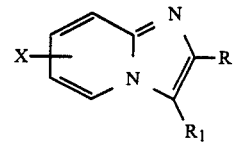  I where

X may be hydrogen, one or more of halogen, hydroxy, alkoxy having 1–3 carbon atoms, benzyloxy, or $C_1$–$C_6$ alkyl.

R may be H or Ar, $R_1$ may be H, $CH_3$ or Ar;

Ar may be

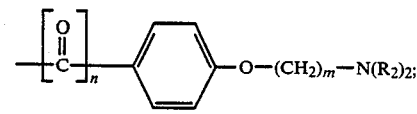

$R_2$ may be a $C_1$–$C_6$ alkyl;

n may be 0 or 1 when R is Ar; or n may be 1 when $R_1$ is Ar is bonded at C-3; and m may be 2–6, with the provision that both R and $R_1$ cannot be Ar at the same time.

The compounds of formula 1 are useful as local anesthetic compounds.

DETAILED DESCRIPTION OF THE INVENTION

The invention in its broadest aspects relates to 2- or 3- aryl substituted imidazo[1,2-a]pyridine compounds which have local anesthetic activity in mammals. The 2- or 3- aryl substituted imidazo[1,2-a]pyridine compounds of the invention demonstrating local anesthetic activity are shown above.

The preferred compounds of the present invention are those wherein X is hydrogen, bromo, hydroxy, benzyloxy, methyl or dimethyl; $R_2$ is butyl; and m is 3.

The 2-aryl substituted imidazo[1,2-a]pyridine compounds where n is 0 are prepared in accordance with Scheme 1.

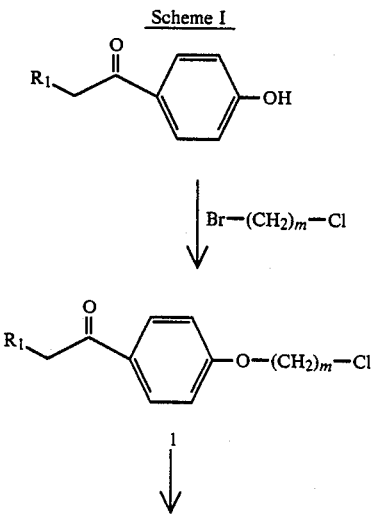

-continued
Scheme I

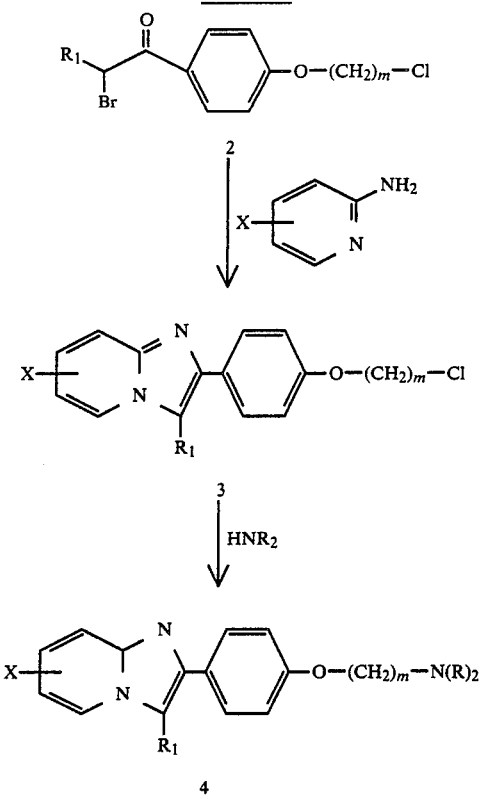

In Scheme I, p-hydroxyacetophenone or p-hydroxypropiophenone, $R_1$ is H or $CH_3$ respectively, is treated with a 1-bromo-ω-chloro alkane such as 1-bromo-2-chlorethane, 1-bromo-3-chloropropane, 1-bromo-4-chlorobutane or 1-bromo-5-chloropentane or 1-bromo-6-chlorohexane by refluxing in an alcoholic base for about 12 to 48 hours to produce a p-chloroalkoxyphenone 1 as a liquid. The alcohol is preferably methanol, and the base may be potassium hydroxide or sodium hydroxide.

The p-chloroalkoxyphenone 1 is then reacted with bromine in either an ether solvent or glacial acetic acid or carbon disulfide. Suitable ethers include tetrahydrofuran, diethyl ether, or dimethoxy ether. The reaction takes place at a temperature of about 10° C. to 65° C. for about 2 to 24 hours to produce α-bromo-ketone 2.

The α-bromoketone 2 is then subjected to a condensation reaction with 2-aminopyridine or a substituted 2-aminopyridine in an alcoholic solvent. The condensation is conducted at about 65° C. to 86° C. for about 2 to 24 hours to yield the chloroalkoxyphenyl imidazopyridine 3. Suitable substituted 2-aminopyridines which may be utilized in the condensation reaction include 3-methyl-2-aminopyridine, 5-bromo-2-aminopyridine, 4-methyl-2-aminopyridine, 3-benzyloxy-2-aminopyridine, 3-hydroxy-2-aminopyridine, and 4,6-dimethyl-2-aminopyridine. The alcoholic solvent may be methanol, ethanol or isopropanol.

The chloroalkoxyphenyl imidazopyridine 3 is treated with an amine solvent, such as dimethylamine, diethylamine, dipropylamine, dibutylamine, dipentylamine or dihexylamine at about 100° C. to 150° C. for 4 to 64 hours to yield the 2-aryl substituted imidazo-[1,2-a]pyridine 4.

The 2-aryl substituted imidazo pyridines where n is 1 are produced according to Scheme II.

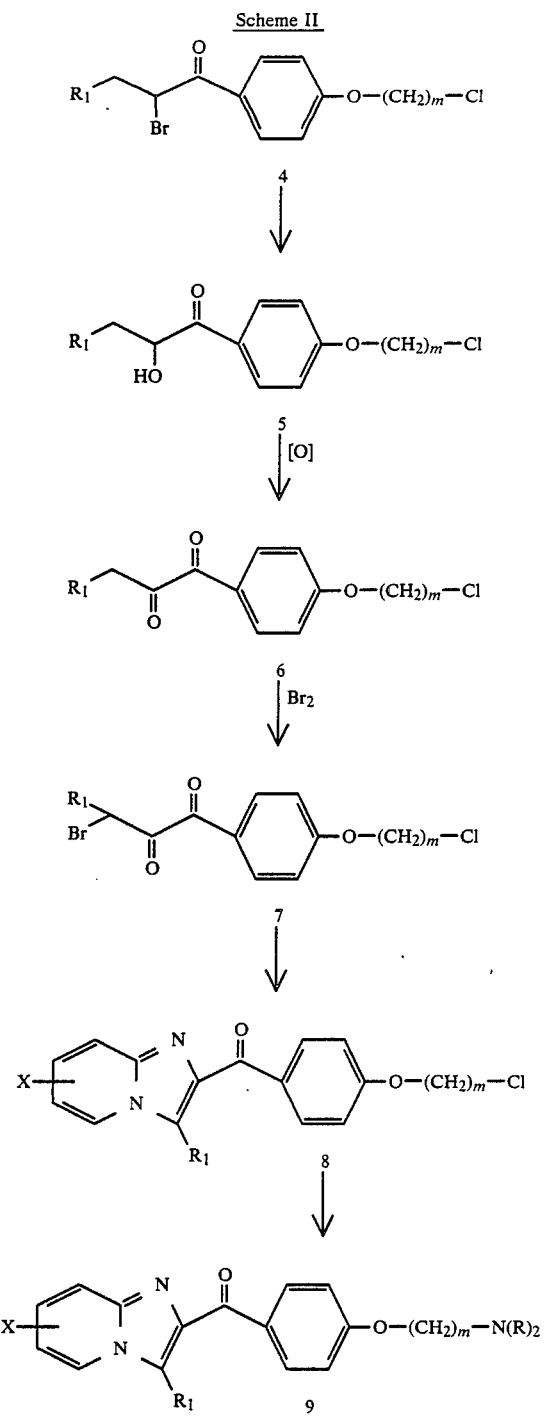

The α-bromoketone 4 which may be prepared as described in Scheme I, is treated in a polar solvent with an aqueous solution of a base, such as sodium hydroxide, at about 20° C. to 50° C. to produce α-hydroxyketone 5. Suitable polar solvents include dimethylformamide, dimethyl sulfoxide, hexamethyl phosphoramide and N-methyl pyrrodlidone.

The α-hydroxyketone 5 is then oxidized with an oxidizing agent, such as pyridinium chlorochromate, chromium trioxidepyridine, dimethyl sulfoxide-oxalyl chloride or chromic acidsulfuric acid, in an inert solvent to yield the diketone 6. Suitable inert solvents include methylene chloride, chloroform and acetone.

The diketone 6 is reacted with bromine in either an ether solvent or glacial acetic acid or carbon disulfide at about 10° C. to 65° C. for about 2 to 24 hours to produce the α-bromodiketone 7. Suitable ethers include tetrahydrofuran, diethyl ether or dimethoxyether.

The α-bromodiketone 7 is subjected to the condensation as previously described in Scheme 1 to produce compound 8 which is reacted with an amine solvent as described in Scheme I to yield the 2-aryl substituted imidazo[1,2-1]pyridines 9.

The 3-aryl substituted imidazo[1,2-a]pyridines where n is 1 are produced in accordance with Scheme III which follows.

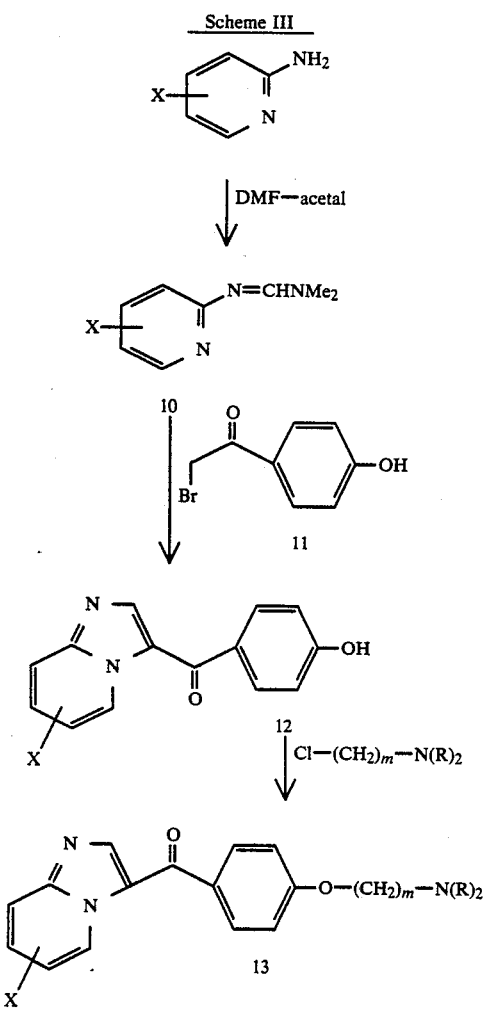

In Scheme III, 2-aminopyridine or a substituted 2-aminopyridine, such as 3-methyl-2-aminopyridine, 5-bromo-2-aminopyridine, 4-methyl-2-aminopyridine or 3-hydroxy-2-aminopyridine reacted with dimethylformamide dimethylacetal or triethyl orthoformate in an inert solvent at about 60° C. to 120° C. for about 4 to 12 hours to produce an amidine 10. Suitable inert solvents include benzene, toluene, xylenes or acetone.

The amidine 10 is then subjected to a condensation reaction with a α-bromoketone 11 in an alcoholic solvent, such as methanol, ethanol or isopropanol at about 60° C. to 85° C. for about 2 to 24 hours to yield a 3-aryl substituted imidazopyridine 12 which is a solid. The α-bromoketone 11 can be produced by reacting p-hydroxy- acetophenone with bromine in either an ether solvent or glacial acetic acid or carbon disulfide at a temperature range of about 10° C. to 65° C. for approximately 2 to 24 hours. Suitable ethers include tetrahydrofuran, diethyl ether or dimethoxy ether.

The 3-aryl substituted imidazopyridine 12 is alkylated with a chloroalkyl dialkylamine to yield the 3-aryl substituted imidazo-[1,2-a]pyridine 13. The reaction is conducted in an alcoholic base such as potassium hydroxide in methanol and in the presence of catalytic iodine at a temperature of about 60° C. to 80° C. for about 8 to 9 hours. The chloroalkoxy dialkylamine used in the reaction is prepared by treating a 1-bromo-ω-chloroalkane with a dialkylamine at about 100° C. to 150° C.

For topical administration, the carrier may take a wide variety of forms depending on the form of preparation, such as creams, dressings, gels, lotions, ointments or liquids. The 2- or 3- aryl substituted imidazo[1,2-a]pyridine will be present in the pharmaceutical composition from about 1% by weight to about 10% by weight, depending on the particular form employed.

An injectable form of the 2- or 3- aryl substituted imidazo-[1,2-a]pyridine is usually administered intradermally, subcutaneously, or submucosally across the path of nerves supplying the area to be anethesized. The injection may also be given intramuscularly. The 2- or 3- aryl substituted imidazo-[1,2-a]pyridines will be present in injectable pharmaceutical composition from about 0.1% by weight to 10% by weight. The injectable preparation may also contain isotonicity adjusting agents such as sodium chloride, pH adjusting agents such as hydrochloric acid and preservatives such as methylparaben. Injectable preparations may be in the form of solutions or suspensions.

Pharmaceutical compositions containing a compound of the present invention as the active ingredient in intimate admixture with a pharmaceutical carrier can be prepared according to conventional pharmaceutical compounding techniques.

The following examples describe the invention in greater particularity and are intended to be a way of illustrating but not limiting the invention.

EXAMPLE 1

2-(4-Dibutylaminopropoxyphenyl)imidazo[1,2-a]pyridine

To a mixture of p-hydroxyacetophenone (50.7 g, 0.37 mol) and 1-bromo-3-chloropropane (160 ml, 1.5 mol) in methanol (250 ml) was added portionwise potassium hydroxide (63 g, 1.12 mol). The mixture was stirred at reflux for 24 hours, cooled to room temperature, filtered through Celite and evaporated in vacuo. The residual semi-solid was diluted with diethyl ether (500 ml) and washed with $H_2O$ (2×300 ml). The ether solution was dried over $MgSO_4$, filtered and evaporated in vacuo to give p-chloropropoxy acetophenone as a liquid in 68% yield (53.38 g). $^1H$ NMR ($CDCl_3$): δ7.98–7.89 (d, J=8.9 Hz, 2H), 7.02–6.92 (d, J=8.9 Hz, 2H), 4.16 (t, J=5.9 Hz, 2H), 3.75 (t, J=6.4 Hz, 2H), 2.52 (s, 3H), 2.34–2.16 (m, 2H).

To a stirred solution of p-chloropropoxyacetophenone (53.3 g, 0.25 mol) in diethyl ether (250 ml) was slowly added bromine (13 ml, 0.25 mol) and allowed to stir at room temperature for 16 hours. The dark mixture was poured into an aqueous saturated sodium bicarbonate solution (300 ml) and the organic layer separated. The ether layer was washed with an aqueous saturated sodium bicarbonate solution (300 ml) and with water (300 ml) and dried over $MgSO_4$. The solution was filtered and evaporated in vacuo to yield α-bromo-4-chloropropoxy acetophenone (64.4 g, 88% yield) as a dark oil. $^1$H NMR ($CDCl_3$): δ7.96 (d, J=8.9 Hz, 2H), 6.95 (d, J=8.9 Hz, 2H), 4.41 (s, 2H), 4.19 (t, 2H), 3.75 (t, 2H), 2.26 (m, 2H).

A mixture of α-bromo-4-chloropropoxy acetophenone (12.8 g, 44 mmol) and 2-aminopyridine (4.0 g, 44 mmol) in ethanol (80 ml) was stirred at reflux for 3 hours, cooled at room temperature and filtered to give 2-(4-chloropropoxyphenyl)imidazo[1,2-a]pyridine (5.2 g, 32% yield) as a white solid. $^1$H NMR ($CD_3OD$): δ8.81 (d, J=6.7 Hz, 1H), 8.51 (s, 1H), 7.97–7.01 (m, 7H) 4.19 (t, J=5.9 Hz, 2H), 3.79 (t, J=6.3 Hz, 2H), 2.25 (m, 2H).

A suspension of 2-(4-chloropropoxyphenyl-)imidazo[1,2-a]-pyridine (5.2 g, 14 mmol) in dibutylamine (30 ml) was stirred at reflux for 5 hours. The excess dibutylamine was removed by distillation and the resulting oil was flash chromatographed (silica gel, 9:1 $CH_2Cl_2$: acetone) to give the free base of the title compound (5.1 g, 93% yield) as an oil. The HCl salt was prepared by dropwise addition of concentrated hydrochloric acid to a solution of the free base in methanol, concentrated and recrystallized from methanol acetone to yield 2-(4-dibutylaminopropoxyphenyl)imidazo-[1,2-a]pyridine as a white crystalline solid, mp 179° C. to 183° C. IR(KBr): 3400, 2620, 1650, 1620 cm$^{-1}$. MS: 380 (MH+). $^1$H NMR ($CD_3OD$): δ8.80 (d, J=8 Hz, 1H), 8.52 (s, 1H), 7.92–7.49 (m, 5H), 7.18 (d, J=8 Hz, 2H), 4.23 (t, J=4.6 Hz, 2H), 3.50–3.13 (m, 6H), 2.25 (m, 2H), 1.82–1.34 (m, 8H), 1.01 (m, 6H).

Theor. $C_{24}H_{33}N_3O.3HCl$: C, 58.95; H, 7.42; N, 8.59. Found: C, 59.25; H, 7.71; N, 9.03.

When in the above procedure, p-hydroxypropiophenone is employed as the starting material, 2-(4-dibutylaminopropoxy-phenyl)-3-methylimidazo [1,2-a]pyridine is obtained as the resultant product.

EXAMPLE 2

2-(4-Dibutylaminopropoxyphenyl)-8-methylimidazo[1,2-a]pyridine

The title compound was prepared as described above by reacting 3-methyl-2-aminopyridine (6.3 g, 15.8 mmol) with α-bromo-4-chloropropoxyacetophenone. The product was reacted with dibutylamine as described above to produce (2.0 g, 32% yield) of the free base which was converted to the HCl salt, mp 214° C. to 217° C. IR(KBr): 3420, 2960, 1650, 1615 cm$^{-1}$. MS: 393 (M+). $^1$H NMR ($CD_3OD$): δ8.25 (d, J=6 Hz, 1H), 8.06 (s, 1H), 7.88 (d, J=7 Hz, 2H), 7.05 (m, 3H), 6.85 (t, J=6 Hz, 1H), 4.13 (t, J=4 Hz, 2H), 3.00–2.80 (m, 6H), 2.59 (s, 3H), 2.10 (m, 2H), 1.57–1.44 (m, 8H), 1.04 (m, 6H).

Theor. $C_{25}H_{35}N_3O.3HCl$: C, 59.70; H, 7.62; N, 8.35. Found: C, 59.61; H, 7.69; N, 8.37.

EXAMPLE 3

2-(4-Dibutylaminopropoxyphenyl)-6-bromoimidazo[1,2-a]pyridine

5-Bromo-2-aminopyridine (2.0 g, 12 mmol) was reacted with α-bromo-4-chloropropoxyacetophenone as described in Example 1. The resulting product was reacted with dibutylamine as described in Example 1 to give the free base of the title compound (2.1 g, 74% yield) which was converted to the HCl salt, mp 193° C. to 195° C. IR(KBr): 3420, 2700, 1650, 1605 cm$^{-1}$. MS: 358 (M+). $^1$H NMR ($CD_3OD$): δ9.10 (brs, 1H), 8.49 (s, 1H), 8.13–8.01 (dd, J=1.6, 9.6 Hz, 1H), 7.85 (d, J=9.2 Hz, 3H), 7.13 (d, J=8.8 Hz, 2H), 4.22 (t, J=6 Hz, 2H), 3.24 (m, 6H), 2.29 (m, 2H), 1.66–1.40 (m, 8H). 1.02 (m, 6H).

Theor. $C_{24}H_{32}BrN_3O.2HCl.H_2O$: C, 52.47; H, 6.61; N, 7.65. Found: C, 52.06; H, 6.47; N, 7.50.

When in the above procedure, p-hydroxypropiophenone is employed as the starting material, 2-(4-dibutylaminopropoxyphenyl)-3-methyl-6-bromoimidazo[1,2-a]pyridine is obtained as the resultant product.

EXAMPLE 4

2-(4-Dibutylaminopropoxyphenyl)-7-methylimidazo[1,2-a]pyridine

The title compound was produced in accordance with Example 1 by reacting 4-methyl-2-aminopyridine (1.1 g, 10.3 mmol) with α-bromo-4-chloropropoxyacetophenone and reacting the resulting compound with dibutylamine to yield 1.6 g of the compound (29% yield) the HCl salt, mp 134° C. to 136° C. IR(KBr): 3440, 2640, 2510 cm$^{-1}$. MS: 393 (M+). $^1$H NMR ($CD_3OD$): δ8.63 (d, J=6.7 Hz, 1H), 8.37 (s, 1H), 7.84 (d, J=8.8 Hz, 2H), 7.66 (s, 1H), 7.33 (d, J=6.9 Hz, 1H), 7.17 (d, J=8.8 Hz, 2H), 4.22 (t, J=5 Hz, 2H), 3.39–3.13 (m, 6H), 2.60 (s, 3H), 2.28 (m, 2H), 1.76–1.40 (m, 8H), 1.02 (m, 6H).

Theor. $C_{25}H_{35}N_3O.3HCl.2H_2O$: C, 55.71; H, 7.86; N, 7.80. Found: C, 55.57; H, 7.60; N, 7.43.

When is the above procedure, p-hydroxypropiophenone is employed as the starting material, 2-(4-dibutylaminopropoxyphenyl)3,7-dimethylimidazo [1,2-a]pyridine is obtained as the resultant product.

EXAMPLE 5

2-(4-Dibutylaminopropoxyphenyl)-8-hydroxyimidazo[1,2-a]pyridine

3-Hydroxy-2-aminopyridine (3.8 g, 34.4 mmol) was reacted with α-bromo-4-chloropropoxyacetophenone as described in Example 1. The resulting product was reacted with dibutylamine as described in Example 1 to produce 5.7 (69% yield) of the free base of the title compound, which was then converted to the HCl salt, mp 174° C. to 177° C. IR(KBr): 3450, 1640, 1610 cm$^{-1}$. MS: 396 (MH+). $^1$H NMR ($CD_3OD$): δ8.42 (s, 1H), 8.29 (d, J=6 Hz, 1H), 7.87 (d, J=9 Hz, 2H), 7.20 (m, 4H), 4.23 (t, J=6 Hz, 2H), 3.50–3.15 (m, 6H), 2.29 (m, 2H), 1.84–1.29 (m, 8H), 1.02 (m, 6H).

Theor. $C_{24}H_{33}N_3O_2.3HCl.\frac{1}{2}H_2O$: C, 56.09; H, 7.26; N, 8.18. Found: C, 56.00; H, 7.09; N, 7.99.

When in the above procedure, p-hydroxypropiophenone is employed as the starting material, 2-(4-dibutylaminopropoxy-phenyl)-3-methyl-8-hydroxyimidazo[1,2-a]pyridine is obtained as the resultant product.

EXAMPLE 6

2-(4-Dibutylaminopropoxyphenyl)-8 benzyloxyimidazo[1,2-a]pyridine

The title compound, was prepared in accordance with Example 1 by reacting 3-benzyloxy-2-aminopyridine (5.0 g, 25 mmol) with α-bromo-4-chloropropoxyacetophenone and reacting the resulting product with dibutylamine to yield 6.7 of the free base (73% yield) which was converted to the HCl salt, mp 153° C. to 156° C. IR(KBr): 3440, 3960, 1620, cm$^{-1}$. MS: 485 (M+). $^1$H NMR (CD$_3$OD): δ8.46 (s, 1H), 7.87 (d, J=8.8 Hz, 2H), 7.62-7.37 (m, 2H), 7.16 (d, J=8.8 Hz, 2H), 5.49 (s, 2H), 4.22 (t, J=5.8 Hz, 2H) 3.49-3.13 (m, 6H), 2.26 (m, 2H), 1.85-1.27 (m, 8H), 1.02 (m, 6H).

Theor. C$_{31}$H$_{39}$N$_3$O$_2$.2HCl.3/2H$_2$O: C, 63.58; H, 7.57; N, 7.18. Found: C, 63.69; H, 7.52; N, 7.17.

When in the above procedure, p-hydroxypropiophenone is employed as the starting material, 2-(4-dibutylaminopropoxy-phenyl)-3-methyl-8-benzyloxyimidazo[1,2-a]pyridine is obtained as the resultant product.

When in the procedure of Example 6, 4,6-dimethyl-2-aminopyridine pyridine is used in place of 3-benzyloxy-2-aminopyridine, 2-(4-dibutylaminopropoxyphenyl)-5,7-dimethylimidazo[1,2-a]pyridine is obtained as the resultant product.

EXAMPLE 7

2-(4-Dibutylaminopropoxyphenyl)-3,8-dimethylimidazo[1,2-a]pyridine p-Hydroxypropiophenone (50 g, 0.33 mmol) was reacted with 1-bromo-3-chloropropane and the resulting compound reacted with bromine as described in Example 1. The resulting compound was reacted with 3-methyl-2-aminopyridine (1.7 g, 16 mmol) and the product reacted with dibutylamine as described in Example 1 to produce 2.4 g. (62% yield) of the title compound as the HCl salt, mp 202° C. to 204° C. IR(KBr): 3420, 2620, 1650 1605cm$^{-1}$. MS: 408 (M+). $^1$H NMR (CD$_3$OD): δ8.58 (d, J=6.5 Hz, 1H), 7.85-7.71 (m, 3H), 7.48 (t, J=6.7 Hz, 1H), 7.22 (d, J=8.7 Hz, 2H), 4.26 (t, J=5.8 Hz, 2H), 3.52-3.16 (m, 6H), 2.75 (s, 3H), 2.73 (s, 3H), 2.33 (m, 2H), 1.87-1.36 (m, 8H), 1.02 (m, 6H).

Theor. C$_{26}$H$_{37}$N$_3$O.3HCl.H$_2$O: C, 58.37; H, 7.91; N, 7.85. Found: C, 58.20; H, 7.98; N, 7.67.

When in the above procedure, 4,6-dimethyl-2-aminopyridine is used in place of 3-methyl-2-aminopyridine, 2-(4-dibutylaminopro-poxyphenyl)-3,5,7-trimethylimidazo[1,2-a]pyridine is obtained as the resultant product.

When in any of the above procedures, 1-bromo-2-chlorothane, 1-bromo-4-chlorobutane, or 1-bromo-5-chloropentane is used in place of 1-bromo-3-chloropropane, the corresponding 2-(4-dibutylaminoethoxyphenyl)-substituted imidazo[1,2-a]pyridines, 2-(4-dibutylaminobutoxyphenyl)-substituted imidazo[1,2-a]pyridines or 2-(4-dibutylaminopentoxyphenyl)-substituted imidazo[1,2-a]-pyridines are obtained.

When in any of the above procedures, dimethylamine, diethylamine, dipropylamine, dipentylamine or dihexylamine is used in place of dibutylamine, the corresponding 2-(4-dimethyl-, 2-(4-diethyl-, 2-(4-dipropyl-2-4(dipentyl- or 2-(4-dihexylaminopropoxyphenyl)-substituted imidazo[1,2-a]pyridines derivatives are obtained.

EXAMPLE 8

2-(4-Dibutylaminopropoxybenzoyl)-8-methylimidazo[1,2-a]pyridine

To a solution of a α-bromoketone (60 g, 0.20 mol) in dimethylformamide (120 ml) was slowly added an aqueous solution of sodium hydroxide (8.6 g, 0.20 mol, in 50 ml of H$_2$O). The mixture was stirred at room temperature for 30 minutes, diluted with diethyl ether (500 ml) and washed once with H$_2$O (500 ml). The ether layer was dried over MgSO$_4$, filtered and concentrated to give α-hydroxy-(4-chloropropoxy)propiophenone (30.5 g, 65% yield) as a yellow oil. $^1$H NMR (CDCl$_3$): δ7.93 (d, J=8.9 Hz, 2H), 6.98 (d, J=8.9 Hz, 2H), 5.12 (m, 1H), 4.21 (t, J=5.9 Hz, 2H), 3.77 (t, J=6.2 Hz, 2H), 2.28 (m, 2H) 1.46 (d, J=6.9 Hz, 3H).

To a solution of α-hydroxy-(4-chloropropoxy)propiophenone (30.5 g, 0.13 mol) in methylene chloride (250 ml) was added pyridinium chlorochromate (41 g, 0.19 mol) portionwise. The mixture was stirred at room temperature for 24 hours, filtered through Celite and concentrated. The dark oil was taken up in diethyl ether, (500 ml) filtered again through Celite then concentrated to give α-keto-(4-chloropropoxy)propiophenone (18.7 g, 62% yield) as an amber oil. $^1$H NMR (CDCl$_3$): δ8.03 (d, J=8.9 Hz, 2H), 6.96 (d, J=8.9 Hz, 2H), 4.21 (t, J=5.9 Hz, 2H), 3.76 (t, J=6.2 Hz, 2H), 2.51 (s, 3H) 2.27 (m, 2H).

To a solution of α-keto-(4-chloropropoxy)propiophenone (18.7 g, 77.9 mmol) in diethyl ether (300 ml) was added bromine (4 ml, 77.9 mmol) dropwise. The solution was stirred at room temperature for 24 hours then poured into an aqueous saturated sodium bicarbonate solution (500 ml). The organic layer was separated, washed once again with an aqueous sodium bicarbonate solution, dried over MgSO$_4$, filtered and concentrated to give α-bromo-α-keto-(4-chloropropoxy)propiophenone (24.4 g, 98% yield) as an amber oil. $^1$H NMR (CDCl$_3$): δ8.02 (d, J=8.9 Hz, 2H), 6.99 (d, J=8.9 Hz, 2H), 4.40 (s, 2H), 4.23 (t, J=7.5 Hz, 2H), 3.76 (t, J=7.5 Hz, 2H) 2.70 (m, 2H).

A solution of 3-methyl-2-aminopyridine (1.6 g, 14.7 mmol) and β-bromo-α-keto-(4-chloropropoxy)propiophenone (4.7 g, 14.7 mmol) in ethanol (50 ml) was stirred at reflux for 3 hours. The mixture was concentrated and the resulting semi-solid was recrystallized from methanol-acetone to give 2-(4-chloropropoxybenzoyl)-8-methylimidazo[1,2-a]pyridine as an off-white solid (2.4 g, 41% yield). $^1$H NMR (CDCl$_3$): δ9.94 (s, 1H), 9.59 (d, J=7.4 Hz, 1H), 8.21 (d, J=8.8 Hz, 2H), 7.73 (m, 1H), 7.10 (d, J=8.8 Hz, 2H) 6.74 (t, J=6.9 Hz, 1H), 4.25 (t, J=5.7 Hz, 2H), 3.77 (t, J=6.2 Hz, 2H), 2.76 (s, 3H), 2.30 (m, 2H).

A mixture of 2-(4-chloropropoxybenzoyl)-8-methylimidazo-[1,2-a]pyridine (2,4 g, 6.0 mmol) in dibutylamine (30 ml) was stirred at reflux for 8 hours. The excess dibutylamine was removed by distillation and the resulting oil was flash chromatographed (silica gel, acetone) to give the free base of the title compound (2.5 g, 100% yield) as a thick oil. The HCl salt was prepared by dropwise addition of concentrated hydrochloric acid to a solution of the title compound in methanol, concentrated and recrystallized from methanol-acetone, mp 159° C. to 161° C. IR(KBr): 3420, 1650cm$^{-1}$. MS: 421 (M+). $^1$H NMR (CD$_3$OD): δ8.89 (s, 1H), 8.72 (d, J=6.6 Hz, 1H), 8.15 (d, J=8.9 Hz, 2H), 7.89 (d, J=7.3 Hz, 1H), 7.48 (t, J=6.9 Hz, 1H), 7.21 (d, J=8.9 Hz, 2H), 4.29 (t, J=7 Hz, 2H), 3.26 (m, 6H), 2.73 (s, 3H), 2.33 (m, 2H), 1.79-1.35 (m, 8H), 1.02 (m, 6H).

Theor. C$_{26}$H$_{35}$N$_3$O$_2$.3HCl.H$_2$O: C, 56.88; H, 7.34; N, 7.65. Found: C, 56.53; H, 7.00; N, 7.60.

EXAMPLE 9

2-(4-Dibutylaminopropoxybenzoyl)-5,7-dimethylimidazo[1,2-a]pyridine

The title compound was prepared in accordance with Example 8 by reacting 4,6-dimethyl-2-aminopyridine (0.8 g, 6.6 mmol) with β-bromo-α-keto-(4-chloropropoxy)propiophenone and then reacting the resulting product with dibutylamine to yield 1.3 g of the free base (100% yield) which was converted to the HCl salt, mp 106° C. to 108° C. IR(KBr): 3440, 1650 cm$^{-1}$. MS: 435 (M+). $^1$H NMR (CD$_3$OD): δ8.68 (s, 1H), 8.17 (d, J=8.9 Hz, 2H), 7.63 (s, 1H), 7.32 (s, 1H), 7.21 (d, J=8,9 Hz, 2H), 4.30 (t, J=6.2 Hz, 2H), 3.25 (m, 6H), 2.87 (s, 3H), 2.62 (s, 3H) 2.36 (m, 2H), 1.85-1.35 (m, 8H), 1.02 (m, 6H).

Theor. C$_{27}$H$_{37}$N$_3$O$_2$.3HCl: C, 59.50; H, 7.40; N, 7.71. Found: C, 60.02; H, 7.76; N, 7.85.

p EXAMPLE 10

2-(4-Dibutylaminopropoxybenzoyl)-7-methylimidazol[1,2-a]pyridine methylimidazo[1,2-a]pyridine 4-Methyl-2-aminopyridine (1.4 g, 12.5 mmol) was reacted with β-bromo-α-keto-(4-chloropropoxy)propiophenone as described in Example 8. The resulting product was reacted with dibutylamine as described in Example 8 to produce 2.9 g (75% yield) of the free base of the title compound which was converted to the HCl salt, mp 210° C. to 212° C. IR(KBr): 3460, 2640, 1650 cm$^{-1}$. MS: 421 (M+). $^1$H NMR (CD$_3$OD): δ8.89 (s, 1H), 8.77 (d, J=7.5 Hz, 2H), 8.12 (d, J=8.9 Hz, 2H), 7.77 (s, 1H), 7.48 (d, J=7.5 Hz, 2H), 7.20 (d, J=8.9 Hz, 2H), 4.30 (t, J=5.7 Hz, 2H), 3.38-3.16 (m, 6H), 2.65 (s, 3H), 2.35 (m, 2H), 1.81-1.34 (m, 8H), 1.02 (m, 6H).

Theor. C$_{26}$H$_{35}$N$_3$O$_2$.3HCl: C, 58.81; H, 7.21; N, 7.91. Found: C, 58.79; H, 7.00; N, 7.79.

EXAMPLE 11

2-(4-Dibutylaminopropoxybenzoyl)-8-benzyloxyimidazo[1,2-a]pyridine

The title compound was prepared according to Example 8 by reacting 3-benzyloxy-2-aminopyridine (2.2 g, 11 mmol) with β-bromo-α-keto-(4-chloropropoxy)propiophenone and then reacting the resulting product with dibutylamine to produce 1.4 g (52% yield) of the free base which was converted to the HCl salt, mp 171° C. to 174° C. IR(KBr): 3400, 2620, 1660 cm$^{-1}$. MS: 513 (M+). $^1$H NMR (CD$_3$OD): δ8.87 (s, 1H), 8.44 (d, J=7.0 Hz, 1H), 8.12 (d, J=7.0 Hz, 2H), 7.66-7.35 (m, 7H), 7.20 (d, J=7 Hz, 2H), 5.51 (brs, 2H) 4.31 (t, J=5.0 Hz, 2H), 3.41-3.14 (m, 6H), 2.32 (m, 2H), 1.65-1.34 (m, 8H), 1.02 (m, 6H).

Theor. C$_{32}$H$_{39}$N$_3$O$_3$.2HCl.½H$_2$O: C, 64.53; H, 7.11; N, 7.06. Found: C, 64.13; H, 7.22; N, 7.00.

EXAMPLE 12

2-(4-Dibutylaminoproxybenzoyl)-6-bromoimidazo[1,2-a]pyridine

5-Bromo-2-aminopyridine (2.7 g, 15.7 mmol) was reacted with β-bromo-α-keto-(4-chloropropoxy)-propiophenone as described in Example 8. The resulting product was reacted with dibutylamine as described in Example 8 to produce 4.5 g (60% yield) of the free base of the title compound which was converted to the HCl salt, mp 214° C. to 216° C. IR(KBr): 3420, 2600, 2440, 1650 cm$^{-1}$. MS: 442 (M+). $^1$H NMR (CD$_3$OD): δ9.20 (s, 1H), 8.86 (s, 1H), 8.21 (d, J=8.7 Hz, 2H), 8.07-7.80 (m, 2H), 7.17 (d, J=8.7 Hz, 2H), 4.25 (m, 2H), 1.78-1.25 (m, 8H), 0.95 (m, 6H).

Theor. C$_{25}$H$_{32}$BrN$_3$O$_2$.2HCl: C, 53.68; H, 6.13; N, 7.51. Found: C, 53.28; H, 6.30; N, 7.52.

When in the above procedure, 2-aminopyridine or 3-hydroxy-2-aminopyridine is used in place of 5-bromo-2-aminopyridine, 2-(4-dibutylaminopropoxybenzoyl)imidazo[1,2-a]pyridin or 2-(4-dibutylaminopropoxybenzoyl)-8-hydroxyimidazo(1,2-alpyridine is obtained.

When in any of the above procedures of Examples 8, 9, 10, 11 or 12, dimethylamine, diethylamine, dipropylamine, dipentylamine or dihexylamine is used in place of dibutylamine, the corresponding 2-(4-dimethyl-, 2-(4-diethyl-, 2-(4-dipropyl-, 2-(4-dipentyl-, or 2-(4-dihexylaminopropoxybenzoyl)-substituted imidazo[1,2-a]pyridine derivatives are obtained.

EXAMPLE 13

3-(4-Dibutylaminopropoxybenzoyl)-8-methylimidazo[1,2-a]pyridine

To a solution of 3-methyl-2-aminopyridine (5.0 g, 46 mmol) in toluene (60 ml) was added dimethylformamide dimethylacetal (7.9 g, 6.2 mmol) dropwise and stirred at reflux for 6 hours. The mixture was concentrated to give 3-methyl-2-dimethylaminoamidinopyridine as an oil (7.0 g, 94% yield). $^1$H NMR (CDCl$_3$): δ8.33 (s, 1H), 8.12-8.05 (m, 1H), 7.42-7.33 (m, 1H) 6.79 (d,d, J=4.9 Hz, 1H), 3.08 (s, 6H), 2.30 (s, 3H).

A mixture of 3-methyl-2-dimethylaminoamidinopyridine (2.8 g, 17 mmol) and α-bromo-p-hydroxyacetophenone (3.6 g, 17 mmol) in ethanol (10 ml) was stirred at reflux for 2 hours. The mixture was cooled to room temperature and the resulting precipitate was collected by filtration and washed with cold ethanol to give 3-(4-hydroxybenzoyl)-8-methylimidazo[1,2-a]pyridine (2.6 g, 63% yield). $^1$H NMR (DMSO): δ9.68 (d, J=8 Hz, 1H), 8.74 (s, 1H), 8.00-7.61 (m, 4H), 7.21 (d, J=7.2 Hz, 2H), 2.74 (s, 3H).

A mixture of 3-(4-hydroxybenzoyl)-8-methylimidazo[1,2-a]-pyridine (2.3 g, 9.6 mmol), dibutylaminopropyl chloride (6.8 g, 33 mmol) and potassium hydroxide (1.3 g, 23 mmol) in methanol (60 ml) was stirred at reflux for 96 hours. The mixture was concentrated and the resulting oil was flash chromatographed (silica gel, 2.5% methanol in diethyl ether) to give 1.3 g (31% yield) of the free base of the title compound. The HCl salt was prepared by dropwise addition of concentrated hydrochloric acid to a solution of the free base in methanol, concentrated and recrystallized from acetone-ether to give the HCl salt of the title compound as an off-white solid, mp 105° C. to 107° C. IR(KBr): 3440, 2640, 1645, 1605 cm$^{-1}$. MS: 421 (M+). $^1$H NMR (CD$_3$OD): δ9.66 (d, J=8 Hz, 1H), 8.74 (s, 1H), 8.00-7.61 (m, 4H), 7.20 (d, J=7.2 Hz, 2H), 4.29 (t, J=5 Hz, 2H), 3.41-3.15 (m, 6H), 2.75 (s, 3H), 2.31 (m, 2H), 1.80-1.42 (m, 8H), 1.02 (m, 6H).

Theor. $C_{26}H_{35}N_3O_3\cdot 3HCl$: C, 58.81; H, 7.21; N, 7.91.
Found: C, 58.77; H, 7.17; N, 7.98.

EXAMPLE 14

3-(4-Dibutylaminopropoxybenzoyl)-6-bromoimidazo[1,2-a]pyridine

The title compound was prepared according to Example 13 by utilizing 5-bromo-2-aminopyridine (5.0 g, 28.9 mmol) in place of the 3-methyl-2-aminopyridine to produce 1.1 g (8.8% yield) of the free base which was converted to the HCl salt, mp 162° C. to 165° C. IR(KBr): 3430, 2650, 1650, 1610 cm$^{-1}$. MS: 442 (M-$C_3H_7^+$). $^1$H NMR (CD$_3$OD): δ9.92 (m, 1H), 8.66 (s, 1H), 8.23 (d,d, J=9.5, 1.8 Hz, 1H), 8.06–7.95 (m, 3H), 7.18 (d, J=8.9 Hz, 2H), 4.28 (t, J=5.5 Hz, 2H), 3.39–3.14 (m, 6H), 2.32 (m, 2H), 1.80–1.34 (m, 8H), 1.02 (m, 6H).

For $C_{25}H_{32}BrN_3O_2\cdot 3HCl\cdot 2H_2O$ Theor.: C, 47.52; H, 6.22; N, 6.65; Cl, 17.85 Found: C. 47.60; H, 5.68; N, 6.66; Cl, 17.94.

When in the above procedure, 2-aminopyridine, 4-methyl-2-aminopyridine, 3-benzyloxy-2-aminopyridine, 4,6-dimethyl-2-aminopyridine, or 3-hydroxy-2-aminopyridine is used in the starting material, the corresponding 3-(4-dibutylaminopropoxybenzoyl-)imidazo[1,2-a]pyridine, 3-(4-dibutylaminopropoxybenzoyl)-7-methylimidazo [1,2-a]pyridine, 3-(4-dibutylaminopropoxybenzoyl)-8-benzyloxyimidazo [1,2-a]pyridine, 3-(4-dibutylaminopropoxybenzoyl)-5,7-dimethylimidazo[1,2-a]pyridine, or 3-(4-dibutylaminopropoxybenzoyl)-8-hydroxyimidazo[1,2-a]pyridine is obtained.

When in any of the above procedures of Examples 13 and 14, dibutylaminoethyl chloride, dimethylaminopentyl chloride, diethaminobutyl chloride or dipentylaminopropyl chloride is employed as the alkylating agent, the corresponding 3-(4-dibutylaminoethyoxy-, 3-(4-dimethylaminopentoxy-, 3-(4-diethylaminobutoxy-, or 3-(4-dipentylaminopropoxy- benzoyl)-substituted imidazo[1,2-a]pyridines are obtained.

EXAMPLES 15

Local Anesthetic Activity

The local anesthetic activity of the above compounds was determined as follows.

The test compounds were dissolved or suspended in a 0.5% aqueous methylcellulose solution containing 0.4% (v/v) of Tween 80, the polyoxyethylene derivative of a sorbitan ester. Doses of up to 100 mg/kg were administered orally by gavage tube to groups of three male albino overnight-fasted mice (18 to 24 g) which were observed intermittently for one hour. The mice were gently restrained and 0.05 ml of a 1% (w/v) solution or suspension of the test compound was injected into the quadriceps femoris muscle of one hind leg. Five minutes later, the mice are individually placed on a wire mesh screen. The wire mesh screen was then inverted. Compounds that posses local anesthetic activity impaired the ability of the mice to grasp the inverted screen with the injected leg. The response to the test compounds was compared to a similarly treated vehicle control group of mice.

TABLE 1

Local Anesthetic Effects of Representative 2- or 3- Aryl substituted imidazo[1,2-a]pyridines in Overnight-fasted Mice

| Compound (Example) | Concentration (in %) of Compound Causing Local Anesthetic Activity |
|---|---|
| 1 | 0.1 |
| 2 | 0.001 |
| 3 | 1.0 |
| 4 | 0.1 |
| 5 | 1.0 |
| 6 | 0.1 |
| 7 | 0.1 |
| 8 | 1.0 |
| 9 | 1.0 |
| 10 | 1.0 |
| 11 | 0.1 |
| 12 | 1.0 |
| 13 | 0.1 |
| 14 | 0.1 |

What is claimed:

1. A compound of the formula

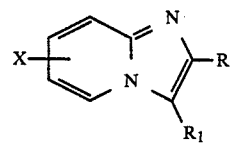

where
X is hydrogen, one or more of halogen, hydroxy, alkoxy having 1–3 carbon atoms, benzyloxy, or $C_1$–$C_6$ alkyl,
R is H or Ar:
$R_1$ is H, CH$_3$ or Ar:
Ar is

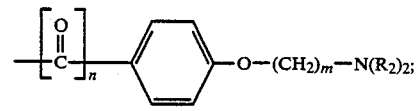

$R_2$ is $C_1$–$C_6$ alkyl;
n is 0 or 1 when R is Ar or 1 when $R_1$ is Ar; and
m is 2–6, with the provision that both R and $R_1$ are not Ar at the same time and that at least one of R and $R_1$ is Ar.

2. A compound of claim 1 wherein X is hydrogen, bromo, hydroxy, benzyloxy, methyl or dimethyl, $R_2$ is butyl and m is 3.

3. A compound of claim 1 selected from the group consisting of 2-(4-dibutylaminopropoxyphenyl-)imidazo[1,2-a]pyridine; 2-(4-dibutylaminopropoxyphenyl)-8-methylimidazo [1,2-a]pyridine; 2-(4-dibutylaminopropoxyphenyl)-6-bromoimidazo [1,2-a]pyridine; 2-(4-dibutylaminopropoxyphenyl)-7-methylimidazo-[1,2-a]pyridine; 2-(4-dibutylaminopropoxyphenyl)-3,8-dimethyl imidazo [1, 2-a]pyridine; 2-(4-dibutylaminopropoxyphenyl)-8-hydroxyimidazo[1,2-a]pyridine; and 2-(4-dibutylaminopropoxyphenyl)-8-benzoyloxyimidazo[1,2-a]pyridine.

4. A compound of claim 1 selected from the group consisting of 2-(4-dibutylaminopropoxybenzoyl)-8-methylimidazo[1,2-a]-pyridine; 2-(4-dibutylaminopropoxybenzoyl)-5,7-dimethylimidazo[1,2-a]pyridine; 2-(4-dibutylaminopropoxybenzoyl)-7-methylimidazo[1,2-a]pyridine; 2-(4-dibutylaminopropoxybenzoyl)-8-benzyloxyimidazo[1,2-a]pyridine; and 2-(4-dibutylaminopropoxybenzoyl)-6-bromoimidazo[1,2-a]pyridine.

5. A compound of claim 1 selected from the group consisting of 3-(4-dibutylaminopropoxybenzoyl)-8-methylimidazo[1,2-a]-pyridine and 3-(4-dibutylaminopropoxybenzoyl)-6-bromoimidazo[1,2-a]pyridine.

* * * * *